US011467029B2

(12) United States Patent
Wingren

(10) Patent No.: US 11,467,029 B2
(45) Date of Patent: *Oct. 11, 2022

(54) LIGHT EXPOSURE MONITORING SYSTEM

(71) Applicant: BrainLit AB, Lund (SE)

(72) Inventor: Tord Wingren, Lomma (SE)

(73) Assignee: BrainLit AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,168

(22) Filed: Feb. 26, 2021

(65) Prior Publication Data

US 2021/0181014 A1 Jun. 17, 2021

Related U.S. Application Data

(63) Continuation of application No. 16/922,384, filed on Jul. 7, 2020, now Pat. No. 10,962,410, which is a continuation of application No. PCT/EP2020/058166, filed on Mar. 24, 2020.

(30) Foreign Application Priority Data

Jul. 12, 2019 (EP) ..................... 19185952

(51) Int. Cl.
*G01J 1/42* (2006.01)
*G01J 1/60* (2006.01)
*G01J 1/02* (2006.01)
*G01J 1/44* (2006.01)

(52) U.S. Cl.
CPC ........... *G01J 1/4204* (2013.01); *G01J 1/0271* (2013.01); *G01J 1/44* (2013.01); *G01J 1/60* (2013.01); *G01J 2001/4266* (2013.01)

(58) Field of Classification Search
CPC .... G01J 1/44; G01J 1/4204; G01J 1/60; G01J 1/32; G01J 1/0271; G01J 1/0242; G01J 2001/4266
See application file for complete search history.

(56) References Cited

U.S. PATENT DOCUMENTS

| 8,531,134 | B2 | 9/2013 | Chemel |
| 8,795,344 | B2 | 8/2014 | Baaijens |
| 9,636,520 | B2 * | 5/2017 | Pedersen ............... A61M 21/00 |
| 10,257,914 | B2 | 4/2019 | Sato |
| 11,006,504 | B2 * | 5/2021 | Van Der Poel ........ H05B 47/16 |

(Continued)

FOREIGN PATENT DOCUMENTS

| WO | 2019105885 A1 | 6/2019 |
| WO | 2019107060 A1 | 6/2019 |

OTHER PUBLICATIONS

International Search Report from International Application No. PCT/EP2020/058166, dated May 28, 2020.
Extended European Search Report dated Jan. 3, 2020.

*Primary Examiner* — Sang H Nguyen
(74) *Attorney, Agent, or Firm* — Brundidge & Stanger, P.C.

(57) ABSTRACT

The present disclosure relates to a light exposure monitoring system that includes a central control server; a plurality of indoor light exposure zones and a positioning system configured to communicate with the central control server to determine: a position (P) of an individual within the plurality of indoor light exposure zones, and a distance between a head of the individual and a floor within the plurality of indoor light exposure zones 18 Claims, 2 Drawing Sheets

(56) References Cited

U.S. PATENT DOCUMENTS

| | | | |
|---|---|---|---|
| 2007/0258243 A1* | 11/2007 | Segall | A61B 90/30 |
| | | | 362/276 |
| 2010/0301776 A1 | 12/2010 | Feri | |
| 2011/0160881 A1 | 6/2011 | Grey | |
| 2014/0055040 A1 | 2/2014 | Nishigaki | |
| 2016/0219675 A1 | 7/2016 | Wingren | |
| 2016/0270656 A1 | 9/2016 | Samec | |
| 2017/0374726 A1 | 12/2017 | Sato | |
| 2018/0043130 A1 | 2/2018 | Moore Ede | |
| 2018/0318601 A1* | 11/2018 | Ciccarelli | A61N 5/0618 |
| 2019/0192710 A1 | 6/2019 | Andersson | |
| 2019/0350066 A1* | 11/2019 | Herf | H05B 47/105 |

\* cited by examiner

LIGHT EXPOSURE MONITORING SYSTEM

CROSS-REFERENCE TO THE RELATED APPLICATION

The present application is a Continuation Application of application Ser. No. 16/922,384, filed Jul. 7, 2020, which claims priority from PCT/EP2020/058166, filed Mar. 24, 2020, the contents of which are incorporated herein by reference.

TECHNICAL FIELD

The present invention relates to a light exposure monitoring system.

BACKGROUND OF THE INVENTION

Light is essential for the well-being of humans and animals. For instance, light affects the circadian rhythm and especially natural light helps individuals to regulate the sleep-wake cycle.

With the development of artificial light sources, such as light emitting diodes, specifically designed light sources have been made possible. It is, for example, possible to simulate natural light cycles in indoor environments. The indoor environments can therefore be tailored to each individual's needs (e.g. having increased levels of blue light in order to treat seasonal affective disorder). However, individuals are typically present in different indoor environments having different lighting conditions. It can therefore be difficult to determine the light a user has been exposed to during a day.

A solution is to equip each user with a personal sensor that can measure and store ambient light levels. However, in most situations it is impractical, or even impossible, to carry a personal light sensor. A solution relying on personal light sensors also leads to a significant increase in related economic costs and device administration. For example, each user must bring the light sensor with him/her and make sure that it is activated, has enough battery charge, and that it is carried such that ambient light can be sensed.

Thus, there exists a need for an improved monitoring of light exposure for individuals.

SUMMARY OF THE INVENTION

In view of the above, it is an object of the present inventive concept to provide a light exposure monitoring system.

It is an object to mitigate, alleviate or eliminate one or more of the above-identified deficiencies in the art and disadvantages singly or in any combination and solve at least the above-mentioned problem.

According to a first aspect a light exposure monitoring system is provided. The light exposure monitoring system comprises: a central control server; a plurality of indoor light exposure zones, each indoor light exposure zone comprising one or more light sources, each light source is configured to send illumination data to the central control server; and a positioning system configured to communicate with the central control server and to determine: a position of an individual within the plurality of indoor light exposure zones, and a distance between a head of the individual and a floor within the plurality of indoor light exposure zones; wherein the central control server is configured to: determine in which indoor light exposure zone among the plurality of indoor light exposure zones the individual is presently located based on the determined position of the individual, determine light exposure data for the indoor light exposure zone, in which the individual is determined to be presently located in, based on the illumination data received from the one or more light sources of the indoor light exposure zone in which the individual is determined to be presently located and the determined distance between the head of the individual and the floor of the indoor light exposure zone in which the individual is determined to be presently located, and accumulate the light exposure data to an actual light profile for the individual.

Within the context of this disclosure, "illumination data" should be construed as information relating to light. For example, illumination data may comprise information relating to an intensity and/or a spectral distribution of light.

Within the context of this disclosure, "light exposure data" should be construed as information relating to light to which the individual, e.g. the eyes of the individual, is exposed to. For example, the light exposure data may be a weighted average of illumination data from a plurality of light sources in the indoor light exposure zone. The weights in the weighted average may be based on a position of each light source in the plurality of light sources.

Within the context of this disclosure, "light exposure zone" should be construed as a space in which the one or more light sources are present. The light exposure zone may be a room or a plurality of rooms. The light exposure zone may be a portion of a room. Within a light exposure zone, light exposure data may vary less than a predetermined value. The predetermined value may relate to an intensity and/or a spectral distribution of light.

Within the context of this disclosure, "actual light profile" should be construed as data associated with an accumulated amount of light that the individual has been exposed to.

By means of the present light exposure monitoring system, accumulation of light exposure data relating to an individual without a need for the individual to carry a light sensor is allowed. Further, the present light exposure monitoring system allows for the accumulation of light exposure data relating to an individual moving in between different indoor light exposure zones without a need for the individual to carry a light sensor. Further the present light exposure monitoring system allows for a light exposure of an individual in an indoor light exposure zone without using a portable and/or stationary light sensor. Thus, the present inventive concept allows for a less complex light exposure system.

Typically, a spatial distribution of light which the individual is exposed to varies with height, e.g. the distance above the floor or above the ground. Hence, the light exposure of the individual will also depend on the distance between the head of the individual and the floor and/or the ground. Since the distance between the head of the individual and the floor/ground may vary (e.g., the individual may change position from standing to sitting and/or laying down), the present light exposure monitoring system allows for an improved determination of light exposure data by taking the distance between the head of the individual and the floor into account, thereby allowing for an enhanced actual light profile for the individual.

The positioning system may comprise: one or more distance sensors configured to determine the distance between the head of the individual and the floor of the indoor light exposure zone in which the individual is determined to be presently located.

The one or more distance sensors may comprise one or more of a radar sensor, a LIDAR sensor, a camera, a time-of-flight camera, and a stereo camera.

An associated advantage is that the distance between the head of the individual and the floor may be determined with a higher precision, thereby allowing for an enhanced actual light profile for the individual.

The positioning system may be further configured to determine a direction in which the individual is facing, and wherein the central control server may be further configured to determine light exposure data further based on the direction in which the individual is facing.

The spatial distribution of light which the individual is exposed to may further vary depending on which direction the individual is facing. Hence, by taking the direction in which the individual is facing into account, the determination of light exposure data may be further improved, thereby allowing for a further enhanced actual light profile of the individual.

The light exposure monitoring system may further comprise: one or more eye sensors configured to communicate with the central control server and to determine a size of a pupil of an eye of the individual; and wherein the central control server may be further configured to determine light exposure data further based on the size of the pupil of the eye of the individual.

Since many effects on the individual due to light exposure may be related to light absorption in the individual's eye, improved light exposure data may be determined by taking the size of the pupil of the eye of the individual into account, thereby allowing for an enhanced actual light profile of the individual. The enhanced actual light profile may better reflect an effect of the light exposure of the individual by taking the size of the pupil of the eye of the individual into account when determining light exposure data.

The one or more eye sensors may comprise optical sensors. The optical sensor may, e.g., comprise a camera. The positioning system may comprise: one or more optical detectors configured to communicate with the central control server, each optical detector being associated with a position within the plurality of indoor light exposure zones. The one or more optical detectors may be configured to detect the individual, thereby determining the position of the individual.

The position of the individual may thereby be determined without a need for the individual to carry a personal identification device. A less complex light exposure system may therefore be allowed.

The positioning system may comprise: one or more electronic devices, each electronic device being associated with a position within the plurality of indoor light exposure zones; and a portable device associated with the individual, the portable device being configured for wireless communication with the one or more electronic devices. The position of the individual may be determined based on the wireless communication between the one or more electronic devices and the portable device.

An associated advantage is that the position of the individual may be determined in a less complex and reliable manner.

The one or more electronic devices may be further configured for wireless communication with the central control server, and the central control server may be further configured to determine the position of the individual based on the wireless communication between the one or more electronic devices and the portable device.

An associated advantage is that the portable device carried by the individual may not need processing capabilities, thereby having a reduced power consumption.

The portable device may be further configured to communicate with the central control server, and to determine the position of the individual based on the wireless communication between the one or more electronic devices and the portable device.

An associated advantage is that processing related to determination of the position of each individual in a plurality of individuals may be distributed to a plurality of portable devices, thereby reducing processing load of the central control server.

The one or more light sources may comprise adjustable light sources.

An associated advantage is that a light environment in one or more indoor light exposure zones in the plurality of indoor light exposure zones may be adjusted. The light environment in one or more indoor light exposure zones in the plurality of indoor light exposure zones may thereby be set to an individual's needs or preferences.

A spectrum and/or a brightness of the one or more light sources may be adjustable. Each of the one or more light sources may be independently adjustable.

An associated advantage is that an improved adjustment of a light environment in one or more indoor light exposure zones in the plurality of indoor light exposure zones may be allowed.

The central control server may be further configured to adjust the one or more light sources.

An associated advantage is that the one or more light sources may be automatically adjusted. The central control server may adjust the one or more light source based on the actual light profile of the individual and/or on a target light profile of the individual. By "target light profile" here is meant a preferred light dose that the individual should accumulate over time. The central control server may thereby automatically adjust the one or more light sources based on the actual light profile of the individual and/or the target light profile of the individual, thereby allowing for an automatic individually adjusted light environment in the indoor light exposure zone.

The positioning system may be further configured to determine a position for each individual in a plurality of individuals.

An associated advantage is that the light exposure monitoring system may service a plurality of individuals.

The positioning system may further comprise a plurality of portable devices, each portable device being associated with an individual in a plurality of individuals.

An associated advantage is that the light exposure monitoring system may service a plurality of individuals.

The central control server may be further configured to: determine in which indoor light exposure zone among the plurality of indoor light exposure zones each individual in the plurality of individuals is presently located based on the determined position of each individual; determine light exposure data for the indoor light exposure zone, in which each individual in the plurality of individuals is determined to be presently located in, based on the illumination data received from the one or more light sources of the indoor light exposure zone in which each individual is determined to be presently located; and accumulate the light exposure data to an actual light profile for each individual.

An associated advantage is that the light exposure monitoring system may service a plurality of individuals.

The light exposure monitoring system may further comprise: an outdoor light exposure zone; and the central control server may be further configured to: determine light exposure data for the outdoor light exposure zone, in which the individual is determined to be presently located, based on illumination data associated with the outdoor light exposure zone.

An associated advantage is that the light exposure monitoring system may account for periods during which the individual is outdoors, thereby allowing for an improved actual light profile of the individual.

The illumination data associated with the outdoor light exposure zone may be based on local weather data received from a weather service provider.

An associated advantage is that illumination data associated with the outdoor light exposure zone may be determined without a light sensor. For example, by a light sensor worn by the individual or a stationary light sensor positioned in the outdoor light exposure zone. A less complex light exposure monitoring system may thereby be allowed.

The outdoor light exposure zone may comprise a light sensor configured to send illumination data associated with the outdoor light exposure zone to the central control server.

An associated advantage is that an improved determination of illumination data associated with the outdoor light exposure zone may be allowed, thereby allowing for an improved light exposure monitoring system.

According to a second aspect, a method for accumulating light exposure data to an actual light profile for an individual is provided. The method comprising: determining in which light exposure zone among a plurality of light exposure zones the individual is presently located; wherein the plurality of light exposure zones comprises an indoor light exposure zone, the indoor light exposure zone comprising one or more light sources; the method further comprising: determining a distance between a head of the individual and a floor of the indoor light exposure zone in which the individual is determined to be presently located; receiving illumination data for the indoor light exposure zone from the one or more light sources; determining light exposure data for the light exposure zone in which the individual is determined to be presently located, wherein the light exposure data is determined based on the received illumination data from the one or more light sources of the indoor light exposure zone and the determined distance between the head of the individual and the floor of the indoor light exposure zone in case the individual is determined to be presently located in the indoor light exposure zone; and accumulating the determined light exposure data to the actual light profile for the individual.

The above-mentioned features and advantages of the system, when applicable, apply to this second aspect as well. In order to avoid undue repetition, reference is made to the above.

The plurality of light exposure zones may comprise an outdoor light exposure zone, and the method may further comprise: receiving local weather data for the outdoor light exposure zone from a weather service provider; and the light exposure data may be determined based on the received local weather data of the outdoor light exposure zone in case the individual is determined to be presently located in the outdoor light exposure zone.

According to a third aspect, a central control server is provided. The central control server comprises: a control circuitry configured to: receive a position of an individual; receive a distance between a head of the individual and a floor; determine in which light exposure zone among a plurality of light exposure zones the individual is presently located based on the received position of the individual; wherein the plurality of light exposure zones comprises an indoor light exposure zone, the indoor light exposure zone comprising one or more light sources; the control circuitry is further configured to: receive illumination data from the one or more light sources; determine light exposure data for the light exposure zone in which the individual is determined to be presently located in, wherein the light exposure data is determined based on the received illumination data from the one or more light sources of the indoor light exposure zone and the distance between the head of the individual and the floor in case the individual is determined to be presently located in the indoor light exposure zone; and accumulate the light exposure data to an actual light profile for the individual.

The above-mentioned features and advantages of the system and the method, when applicable, apply to this third aspect as well. In order to avoid undue repetition, reference is made to the above.

The plurality of light exposure zones may comprise an outdoor light exposure zone, and the control circuitry may be further configured to: receive local weather data of the outdoor light exposure zone from a weather service provider; and the light exposure data may be determined based on the local weather data received from the weather service provider in case the individual is determined to be presently located in the outdoor light exposure zone.

A further scope of applicability of the present disclosure will become apparent from the detailed description given below. However, it should be understood that the detailed description and specific examples, while indicating preferred variants of the present inventive concept, are given by way of illustration only, since various changes and modifications within the scope of the inventive concept will become apparent to those skilled in the art from this detailed description.

Hence, it is to be understood that this inventive concept is not limited to the particular steps of the methods described or component parts of the systems described as such method and system may vary. It is also to be understood that the terminology used herein is for purpose of describing particular embodiments only and is not intended to be limiting. It must be noted that, as used in the specification and the appended claim, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings do not exclude other elements or steps.

BRIEF DESCRIPTION OF THE DRAWINGS

The above and other aspects of the present inventive concept will now be described in more detail, with reference to appended drawings showing variants of the inventive concept. The figures should not be considered limiting the inventive concept to the specific variant; instead they are used for explaining and understanding the inventive concept.

As illustrated in the figures, the sizes of layers and regions are exaggerated for illustrative purposes and, thus, are provided to illustrate the general structures of embodiments of the present inventive concept. Like reference numerals refer to like elements throughout.

DETAILED DESCRIPTION

The present inventive concept will now be described more fully hereinafter with reference to the accompanying drawings, in which currently preferred variants of the inventive concept are shown. This inventive concept may, however, be implemented in many different forms and should not be construed as limited to the variants set forth herein; rather, these variants are provided for thoroughness and completeness, and fully convey the scope of the present inventive concept to the skilled person.

Figure 1A:
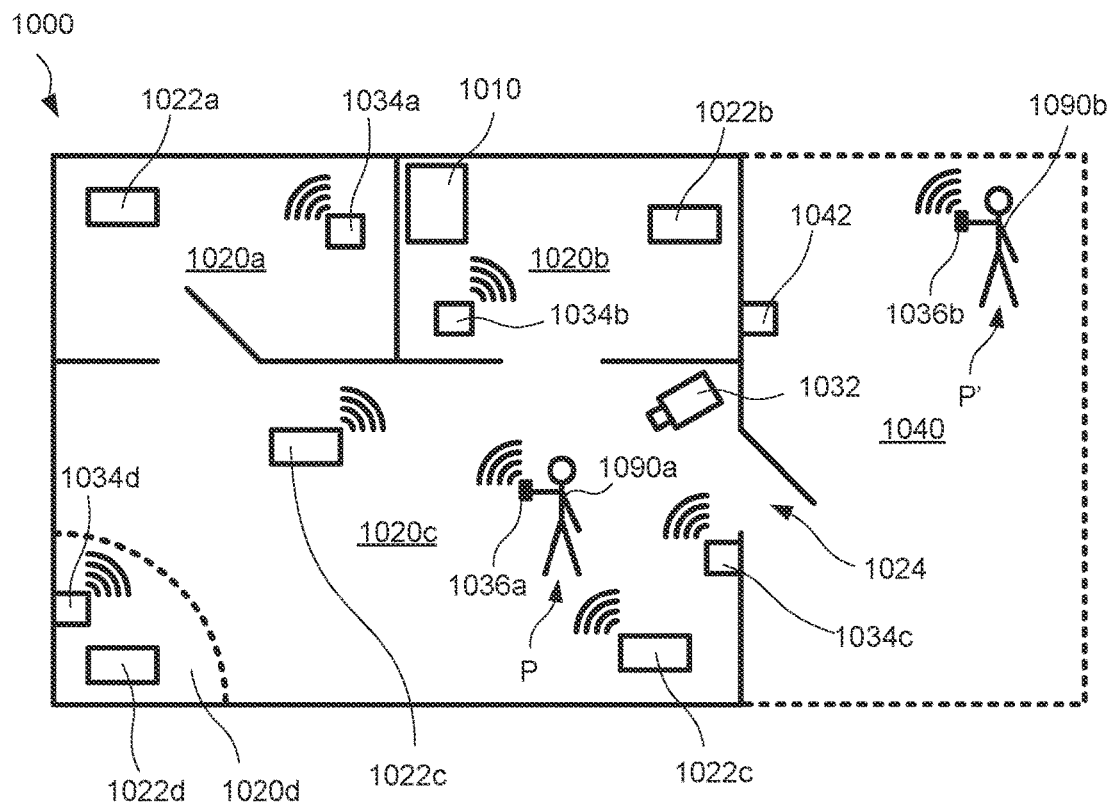
FIG. 1A illustrates a light exposure monitoring system.

FIG. 1A illustrates a light exposure monitoring system 1000. The light exposure monitoring system 1000 comprises a central control server 1010. The central control server 1010 may be a local server arranged in an indoor light exposure zone 1020, as exemplified in FIG. 1A where the central control server 1010 is arranged in an indoor light exposure zone 1020b. The central control server 1010 may be a remote server. The central control server 1010 may be a cloud server.

The light exposure monitoring system 1000 further comprises a plurality of indoor light exposure zones 1020, each indoor light exposure zone 1020 comprising one or more light sources 1022, each light source 1022 is configured to send illumination data to the central control server 1010.

The light exposure monitoring system 1000 may define the plurality of indoor light exposure zones 1020 based on a position of each light source 1022 of the one or more light sources 1022. An indoor light exposure zone 1020 may be separate room, which is exemplified in FIG. 1A by a first room 1020a, a second room 1020b, and a third room 1020c. An indoor light exposure zone 1020 may be a sub-space of a room, which is exemplified in FIG. 1A by a sub-space 1020d in the third room 1020c. Each light source 1022 may be configured to send illumination data to the central control server 1010 via wired and/or wireless communication. Each light source 1022 may be configured to communicate with the central control server 1010 via WIFI, Ethernet, Bluetooth, and/or NFC. The one or more light sources 1022 may be configured to communicate with the central control server 1010 via an internet connection.

The one or more light sources 1022 may comprise adjustable light sources. A light environment in one or more indoor light exposure zones 1020 in the plurality of indoor light exposure zones 1020 may thereby be adjusted. The light environment in one or more indoor light exposure zones 1020 in the plurality of indoor light exposure zones 1020 may thereby be set to an individual's needs or preferences. The one or more light sources 1022 may be configured to send present illumination data to the central control server 1010.

A spectrum and/or a brightness of the one or more light sources 1022 may be adjustable. Each of the one or more light sources 1022 may be independently adjustable. The spectrum and the brightness of each of the one or more light sources 1022 may be individually adjustable. An improved adjustment of the light environment in one or more light exposure zones 1020 in the plurality of light exposure zones 1020 may thereby be allowed.

The light exposure monitoring system 1000 further comprises a positioning system 1030 configured to communicate with the central control server 1010 and to determine a position P of an individual 1090 within the plurality of indoor light exposure zones 1020. The positioning system 1030 may be configured to communicate with the central control server 1010 via WIFI, Ethernet or Bluetooth. The positioning system 1030 may be configured to communicate with the central control server 1010 via an internet connection. In the example shown in FIG. 1A, the positioning system 1030 determines the position P of the individual 1090.

The positioning system 1030 is further configured to determine a distance D between a head of the individual 1090 and a floor within the plurality of indoor light exposure zones 1020. Examples of how the positioning system 1030 may determine the distance D between the head of the individual 1090 and the floor will be described in relation to FIG. 1B.

The positioning system 1030 may, as exemplified in FIG. 1A, comprise one or more optical detectors 1032 configured to communicate with the central control server 1010, each optical detector 1032 being associated with a position within the plurality of indoor light exposure zones 1020. The one or more optical detectors 1032 may be configured to detect the individual 1090, thereby determining the position P of the individual 1090. The position P of the individual 1090 may thereby be determined without a need for the individual 1090 to carry a personal identification device. The positioning system 1030 may be further configured to identify the individual 1090. The positioning system 1030 may comprise processing capabilities configured to identify the individual 1090, and to communicate the identity of the individual 1090 to the central control server 1010. The individual 1090 may be identified by facial recognition. The one or more optical detectors 1032 may comprise one or more cameras and/or one or more image sensors. The one or more optical detectors 1032 may comprise one or more Modcams. A Modcam is an optical detector that uses computer vision to determine movements and profiles of individuals. The one or more optical detectors 1032 may be configured to communicate with the central control server 1010 via a wired and/or wireless connection. Each one or more optical detectors 1032 may be configured to determine a position P of the individual 1090 relative to respective optical detector 1032, and the position P of the individual 1090 may be determined based on the position associated with each optical detector 1032 and the determined position P of the individual 1090 relative to respective optical detector 1032.

The positioning system 1030 may comprise, as exemplified in FIG. 1A, one or more electronic devices 1034, each electronic device 1034 being associated with a position within the plurality of indoor light exposure zones 1020, and a portable device 1036 associated with the individual 1090, the portable device 1036 being configured for wireless communication with the one or more electronic devices 1034. The position P of the individual 1090 may be determined based on the wireless communication between the one or more electronic devices 1034 and the portable device 1036. The position P of the individual 1090 may thereby be determined in a less complex and reliable manner. The one or more electronic devices 1034 may comprise a Bluetooth beacon and/or a WIFI access point. The one or more electronic devices 1034 may be comprised in the one or more light sources 1022, as exemplified in FIG. 1A with light sources 1022c located in the third room 1020c. It is to be understood that more than one electronic device 1034 may be present in the indoor light exposure zone 1020. By having more than one electronic device 1034 in each indoor light exposure zone 1020, a better determination of the position P of the individual 1090 may be allowed. The portable device 1036 may be a wireless token or a wireless tag. The portable device 1036 may be a smartphone, a smartwatch, a tag, a smartring, or a wireless key. The portable device 1036 and the one or more electronic devices 1034 may communicate via WIFI, Bluetooth, RFID and/or NFC. The wireless communication between the portable device 1036 and the one or more electronic devices 1034 may be based on ultra-wideband (UWB) technology, which may allow for a reliable and more precise determination of the position P of the individual 1090. The position P of the individual 1090 may be based on a number of electronic devices 1034 in communication with the portable device 1036. The position P of the individual 1090 may be based on a signal strength, angle-of-arrival information, and/or time-of-arrival, associated with the wireless communication between the one or more electronic devices 1034 and the portable device 1036. Thus, the position P of the individual 1090 may be determined based on the position associated with each of the one or more electronic devices 1034 and relative positions between the portable device 1036 and the one or more electronic devices 1034 in communication with the portable device 1036.

The one or more electronic devices 1034 may be further configured for wireless communication with the central control server 1010, and the central control server 1010 may be further configured to determine the position P of the individual 1090 based on the wireless communication between the one or more electronic devices 1034 and the portable device 1036. The portable device 1036 carried by the individual 1090 may thereby not need processing capabilities, and thus having a reduced power consumption. Thus, any necessary calculations may be performed by the central control server 1010. A less complex light exposure monitoring may thereby be allowed.

The portable device 1036 may be further configured to communicate with the central control server 1010, and to determine the position P of the individual 1090 based on the wireless communication between the one or more electronic devices 1034 and the portable device 1036. The portable device 1036 may be configured to communicate with central control server 1010 via WIFI, Bluetooth, and/or NFC. The portable device 1036 may be configured to communicate with the central control server 1010 via an internet connection. The portable device 1036 may comprise a processor configured to determine the position P of the individual 1090 based on the wireless communication between the one or more electronic devices 1034 and the portable device 1036. Processing related to the determination of the position P of each individual 1090 in a plurality of individuals 1090 may thereby be distributed to a plurality of portable devices 1036, thus reducing processing load of the central control server 1010.

The central control server 1010 is configured to determine in which indoor light exposure zone 1020 among the plurality of indoor light exposure zones 1020 the individual 1090 is presently located based on the determined position P of the individual 1090. In the example shown in FIG. 1A, the central control server 1010 determines that the individual 1090 is presently located in the third room 1020c based on the determined position P of the individual 1090.

The central control server 1010 is further configured to determine light exposure data for the indoor light exposure zone 1020, in which the individual 1090 is determined to be presently located in, based on the illumination data received from the one or more light sources 1022 of the indoor light exposure zone 1020 in which the individual 1090 is determined to be presently located and the determined distance between the head of the individual and the floor of the indoor light exposure zone 1020 in which the individual 1090 is determined to be presently located. Since the light exposure data is based on illumination data received from the one or more light sources 1022, the light exposure data determined by the central control server 1010 may be related to an approximation of light that the individual is exposed to. Thus, the light exposure data determined by the central control server 1010 may be approximation of an actual light exposure of the individual. The light exposure data for the indoor light exposure zone 1020 may be a weighted average of the illumination data received from the one or more light sources 1022 of the indoor light exposure zone 1020 in which the individual 1090 is determined to be presently located. The weights of the weighted average may be similar. The weights of the weighted average may be determined by a calibration of the indoor light exposure zone 1020. For instance, during calibration of the indoor light exposure zone 1020, a contribution of each of the one or more light sources 1022 of the indoor light exposure zone 1020 to the total light environment in the indoor light exposure zone 1020 may be measured, and the weights for each of the one or more light sources 1022 in the weighted average may be based on the measured contribution for respective light source 1022 of the one or more light sources 1022.

The central control server 1010 is further configured to accumulate the light exposure data to an actual light profile for the individual 1090. As the individual 1090 moves between indoor light exposure zones 1020, the light exposure monitoring system 1000 may continuously or intermittently accumulate the light exposure data to the actual light profile for the individual 1090. Thus, the actual light profile for the individual 1090 thereby comprises data related to light environments in which the individual 1090 has been located in. By means of the present light exposure monitoring system 1000, accumulation of light exposure data of an individual 1090 without a need for the individual 1090 to carry a light sensor is allowed. Further, the present light exposure monitoring system 1000 allows for the accumulation of light exposure data of an individual 1090 moving in between different indoor light exposure zones 1020 without a need for the individual 1090 to carry a light sensor.

The central control server 1010 may be further configured to adjust the one or more light sources 1022.

The one or more light sources 1022 may thereby be automatically adjusted by the central control server 1010 (i.e. without input from the individual 1090). The central control server 1010 may adjust the one or more light sources 1022 based on the actual light profile of the individual 1090 and/or on a target light profile of the individual 1090. The central control server 1010 may adjust the one or more light sources 1022 based on a comparison between the actual light profile of the individual 1090 and the target light profile of the individual 1090. The central control server 1010 may adjust the one or more light sources 1022 such that a difference between the actual light profile for the individual 1090 and the target light profile of the individual 1090 is reduced. In other words, the central control server 1010 may adjust the one or more light sources 1022 such that the actual light profile for the individual 1090, over time, approaches, or aligns with, the target light profile. The central control server 1010 may comprise a non-transitory computer-readable storage medium configured to store the actual light profile of the individual 1090 and/or the target light profile of the individual 1090.

The positioning system 1030 may be further configured to determine a position P for each individual 1090 in a plurality of individuals 1090. The positioning system 1030 may further comprise a plurality of portable devices 1036, each portable device 1036 being associated with an individual 1090 in a plurality of individuals 1090.

The central control server 1010 may be further configured to determine in which indoor light exposure zone 1020 among the plurality of indoor light exposure zones 1020 each individual 1090 in the plurality of individuals 1090 is presently located based on the determined position P of each individual 1090.

The central control server 1010 may be further configured to determine light exposure data for the indoor light exposure zone 1020, in which each individual 1090 in the plurality of individuals 1090 is determined to be presently located in, based on the illumination data received from the one or more light sources 1022 of the indoor light exposure zone 1020 in which each individual 1090 is determined to be presently located.

The central control server 1010 may accumulate the light exposure data to an actual light profile for each individual 1090.

Thus, the light exposure monitoring system 1000 may service a plurality of individuals 1090. It is to be understood that the functionality of the light exposure monitoring system 1000 described for an individual 1090 may be applicable for each individual 1090 in the plurality of individuals 1090. In order to avoid undue repetition, reference is therefore made to the above. The central control server 1010 may be further configured to adjust the one or more light sources 1022 based on the actual light profiles for each individual 1090 in the plurality of individuals 1090 and/or target light profiles for each individual 1090 in the plurality of individuals 1090. Each individual 1090 in the plurality of individuals 1090 may be assigned with a priority, and the central control server 1010 may be further configured to adjust the one or more light sources 1022 further based on the priority of each individual 1090 in the plurality of individuals 1090. For instance, in case the central control server 1010 determines that the one or more light sources 1022 should be adjusted differently for two different individuals in the plurality of individuals 1090 based on their respective actual light profiles and/or target light profiles, the central control server 1010 may adjust the one or more light sources 1022 based on the actual light profile and/or the target light profile for the individual 1090 having the highest priority.

The light exposure monitoring system 1000 may further comprise an outdoor light exposure zone 1040, as exemplified in FIG. 1A. The outdoor light exposure zone 1040 may be geographically limited. For instance, the outdoor light exposure zone 1040 may be in a close vicinity of the plurality of indoor light exposure zones 1020. The outdoor light exposure zone 1040 may be a larger area in which the plurality of indoor light exposure zones 1020 is located in, such as a neighborhood or a city.

The central control server 1010 may be further configured to determine light exposure data for the outdoor light exposure zone 1040, in which the individual 1090 is determined to be presently located, based on illumination data associated with the outdoor light exposure zone 1040. The light exposure monitoring system 1000 may thereby account for periods during which the individual 1090 is located outdoors, thus allowing for an improved actual light profile of the individual 1090. The light exposure data for the outdoor light exposure zone 1040 may be associated with ambient light present in the outdoor light exposure zone 1040. A level of ambient light present in the outdoor light exposure zone 1040 may vary depending on time of day, season, and/or weather. For instance, during a summer day, the ambient light may be direct and/or indirect sunlight, while during a winter night, the ambient light may be non-existent. The central control server 1010 may be further configured to determine whether the individual 1090 is in the outdoor light exposure zone 1040 based on the determined position P of the individual 1090. For instance, an exit electronic device 1034c of the positioning system 1030 may be located close to an exit 1024 of an indoor light exposure zone 1020c, and the central control server 1010 may determine that the individual 1090 is located in the outdoor light exposure zone 1040 based on communication between the portable device 1036 and the exit electronic device 1034c. An optical detector 1032 of the positioning system 1030 may be arranged such that the exit 1024 is monitored by the optical detector 1032, thereby allowing the central control server 1010 to determine that the individual 1090 has gone through the exit 1024 and thus is located in the outdoor light exposure zone 1040. In case the positioning system 1030 fails to determine a position P of the individual 1090 (i.e. the portable device 1036 is not in communication with any electronic device 1034 in the plurality of electronic devices 1034, and/or the individual 1090 is not detected by an optical detector 1032) subsequent to determining that the individual 1090 is in the outdoor light exposure zone 1040 (e.g. based on the wireless communication between the portable device 1036 and the exit electronic device 1034c and/or by the optical detector 1032 monitoring the exit 1024), the central control server 1010 may determine that the individual 1090 is still located in the outdoor light exposure zone 1040. It is to be understood that the exit 1024 of the indoor light exposure zone 1020c may be an entrance to the indoor light exposure zone 1020c from the outdoor light exposure zone 1040.

The positioning system 1030 may be further configured to determine an outdoor position P' of the individual 1090. The outdoor position P' of the individual 1090 may be based on a communication between the portable device 1036 and cellphone base stations and/or WIFI access points. For instance, each cellphone base station may be associated with a unique cell-id, and each WIFI access point may be associated with a unique SSID and/or MAC address. During communication between the portable device 1036 and the cellphone base stations and/or WIFI access points, cell-ids, SSID, and/or MAC addresses may be retrieved to the portable device 1036. Upon comparing the retrieved cell-ids, SSID, and/or MAC addresses with a predetermined database comprising cell-ids, SSID, and/or MAC addresses linked with positions of the cellphone base stations and/or WIFI access points, an outdoor position P' of the portable device 1036 (and hence of the individual 1090) may be determined.

The illumination data associated with the outdoor light exposure zone 1040 may be based on local weather data received from a weather service provider. Illumination data associated with the outdoor light exposure zone 1040 may thereby be determined without a light sensor. For instance, a light sensor worn by the individual 1090 or a stationary light sensor positioned in the outdoor light exposure zone 1040 may not be needed. A less complex light exposure monitoring system 1000 may thereby be allowed. The illumination data associated with the outdoor light exposure zone 1040 may further be based on the outdoor position P' and/or a global position of the individual 1090. The global position of the individual 1090 may be a global position of the light exposure monitoring system 1000. The weather service provider may be a third-party weather service provider, which may communicate with the central control server 1010 via the internet. The weather service provider may be a weather station configured to communicate with the central control server 1010. The local weather data may be received from the weather service provider via a wired or a wireless connection.

The outdoor light exposure zone 1040 may comprise a light sensor 1042, as exemplified in FIG. 1A. The light sensor 1042 may be configured to send illumination data associated with the outdoor light exposure zone 1040 to the central control server 1010. An improved determination of illumination data associated with the outdoor light exposure zone 1040 may thereby be allowed, thus allowing for an improved light exposure monitoring system 1000. The outdoor light exposure zone 1040 may comprise a plurality of light sensors 1042. The light exposure data may be based on illumination data received from each of the plurality of light sensors 1042. The light exposure data may be based on a weighted average of the illumination data received from each of the plurality of light sensors 1042. The weights in the weighted average may be based on a position of each light sensor 1042 in the plurality of light sensors 1042. The weights in the weighted average may be similar to each other.

Figure 1B:
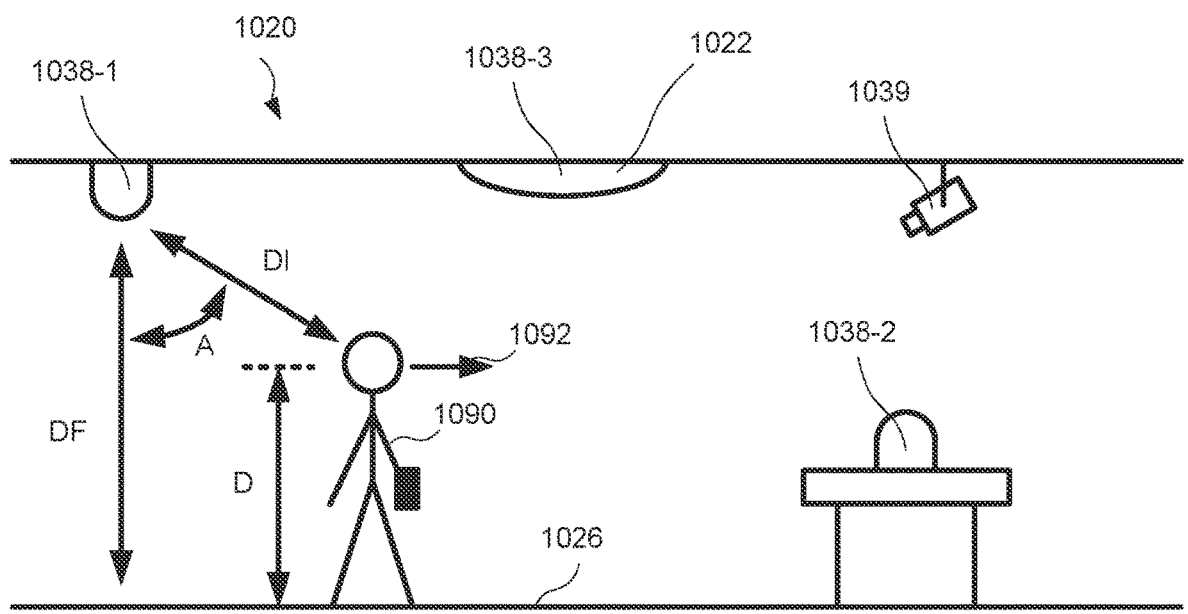
FIG. 1B illustrates an individual in an indoor light exposure zone.

FIG. 1B illustrates the individual 1090 in the indoor light exposure zone 1020. The individual 1090 and/or the indoor light exposure zone 1020 of FIG. 1B may correspond to the individual 1090a and the light exposure zone 1020c discussed in relation to FIG. 1A. Typically, a spatial distribution of light which the individual 1090 is exposed to varies not only between different light exposure zones (as discussed in connection with FIG. 1A), but also with height. For example, the spatial distribution of light which the individual 1090 is exposed to is different depending on if the individual 1090 is standing or sitting. It is therefore important to take the distance D between the head of the individual 1090 and the floor 1026 into account when determining the light exposure data, thereby improving the actual light profile for the individual 1090. A spatial distribution of light in an indoor light exposure zone 1020 may be determined in different manners. For example, the spatial distribution of light in the indoor light exposure zone 1020 having three-dimensional information of the light intensity and spectrum may be determined by simulating and/or numerically determining propagation of light emitted from the one or more light sources 1022 using the illumination data received from the one or more light sources 1022. Alternatively, or additionally, in an installation/commissioning phase of the light monitoring system 1000, a combined spatial distribution and/or individual spatial distributions for the one or more light sources 1022 may be determined using, e.g. a portable light sensor configured to determine an intensity and spectrum of light, and a three-dimensional position of the portable light sensor. Thus, the spatial distribution of the light may be determined having three-dimensional information of the light intensity and spectrum.

As is shown in the example of FIG. 1B, the positioning system 1030 may further comprise one or more distance sensors 1038 configured to determine the distance D between the head of the individual 1090 and the floor 1026 of the indoor light exposure zone 1020 in which the individual 1090 is determined to be presently located. In the example shown in FIG. 1B, the one or more distance sensors 1038 comprises a first distance sensor 1038-1, a second distance sensor 1038-2, and a third distance sensor 1038-3. The first distance sensor 1038-1 and the second distance sensor 1038-2 in this example are standalone devices, while the third distance sensor 1038-3 is integrated in a light source 1022 (e.g., a luminaire). It is to be understood that the one or more distance sensors 1038 may be integrated in other devices. The one or more distance sensors 1038 may be arranged in a plurality of different positions. This is exemplified in FIG. 1B by the first distance sensor 1038-1 being arranged in the ceiling, and the second distance sensor 1038-2 being arranged on a table. The distance D between the head of the individual 1090 and the floor 1026 may be determined using distances and directions between the head of the individual 1090 and the one or more distance sensors 1038, and distances between the one or more distance sensors 1038 and the floor 1026. This is exemplified in FIG. 1B for a first distance sensor 1038-1 at a distance DI and a direction A from the head of the individual 1090. The direction between the first distance sensor 1038-1 and the head of the individual 1090 is in this example represented by an angle A between a line (not shown) connecting the first distance sensor 1038-1 and the head of the individual 1090 and a vertical direction (not shown). A distance DF between the first distance sensor 1038-1 and the floor 1026 may be known from an installation/commissioning phase of the first distance sensor 1038-1 and/or be measured by, e.g., the distance sensor 1038-1. The one or more distance sensors 1038 may comprise one or more of a radar sensor, a LIDAR sensor, a camera, a time-of-flight camera, and a stereo camera.

The positioning system 1030 may be further configured to determine a direction in which the individual 1090 is facing (represented by arrow 1092 in FIG. 1B). The central control server 1010 may be further configured to determine light exposure data further based on the direction in which the individual 1090 is facing. The direction 1092 in which the individual 1090 is facing may be determined by, e.g., using imaging techniques. Such imaging techniques may be configured to identify the face and/or eyes of the individual 1090, thereby determining in which direction 1092 the individual 1090 is facing. The spatial distribution of light which the individual 1090 is exposed to may further vary depending on which direction the individual 1090 is facing (i.e. the intensity and/or spectrum of light that the individual's 1090 eyes are exposed to). Hence, by taking the direction in which the individual 1090 is facing into account, the determination of light exposure data may be further improved, thereby allowing for a further enhanced actual light profile for the individual 1090.

The light exposure monitoring 1000 system may further comprise one or more eye sensors 1039 configured to communicate with the central control server 1010 and to determine a size of a pupil of an eye of the individual 1090. The central control server 1010 may be further configured to determine light exposure data further based on the size of the pupil of the eye of the individual 1090. The determined light exposure data may be scaled by the size of the pupil of the eye of the individual 1090, thereby reflecting an amount of light entering the eye of the individual 1090. Since many effects on the individual 1090 due to light exposure may be related to light absorption in the individual's 1090 eye, improved light exposure data may be determined by taking the size of the pupil of the eye of the individual 1090 into account, thereby allowing for an enhanced actual light profile of the individual 1090. The enhanced actual light profile may better reflect an effect of the light exposure of the individual by taking the size of the pupil of the eye of the individual into account when determining light exposure data.

The one or more eye sensors 1039 may comprise optical sensors. The optical sensor may, e.g., comprise a camera as shown in the example of FIG. 1B.

Figure 2:
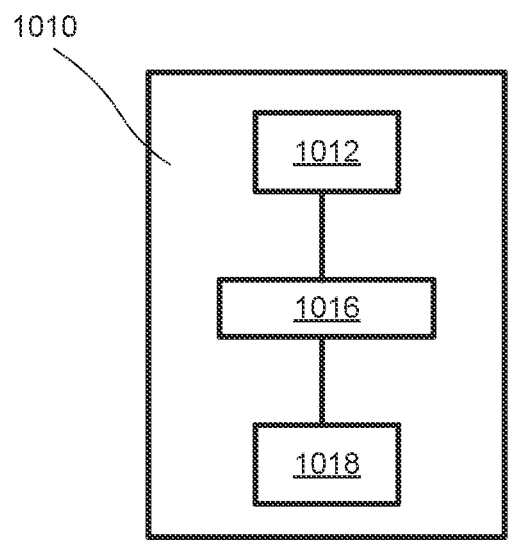
FIG. 2 illustrates a central control server.

FIG. 2 illustrates a central control server 1010. The central control server 1010 comprises a control circuitry 1012. The central control server 1010 may further comprise a non-transitory computer-readable storage medium 1014, as shown in the example in FIG. 2. The control circuitry 1012 and the non-transitory computer-readable storage medium 1014 may communicate via a data bus 1016, as exemplified in FIG. 2.

The control circuitry 1012 is configured to receive a position of an individual.

The control circuitry 1012 is further configured to receive a distance between a head of the individual and a floor.

The control circuitry 1012 is further configured to determine in which light exposure zone among a plurality of light exposure zones the individual is presently located based on the received position of the individual. The plurality of light exposure zones comprises an indoor light exposure zone. The indoor light exposure zone comprises one or more light sources.

The control circuitry 1012 is further configured to receive illumination data from the one or more light sources.

The control circuitry 1012 is further configured to determine light exposure data for the light exposure zone in which the individual is determined to be presently located in. The light exposure data is determined based on the received illumination data from the one or more light sources of the indoor light exposure zone and the distance between the head of the individual and the floor in case the individual is determined to be presently located in the indoor light exposure zone.

The control circuitry 1012 is further configured to accumulate the light exposure data to an actual light profile for the individual. The actual light profile for the individual may be stored on the non-transitory computer-readable storage medium 1014.

The plurality of light exposure zones may comprise an outdoor light exposure zone.

The control circuitry 1012 may be further configured to receive local weather data of the outdoor light exposure zone from a weather service provider, and the light exposure data may be determined based on the local weather data received from the weather service provider in case the individual is determined to be presently located in the outdoor light exposure zone.

Some, or all, of the described functions of the control circuitry 1012 may be software implemented, such functionality may as well be carried out via dedicated hardware, or a combination of hardware and software. Thus, the functions of the control circuitry 1012 may be hardware and/or software implemented.

Figure 3:
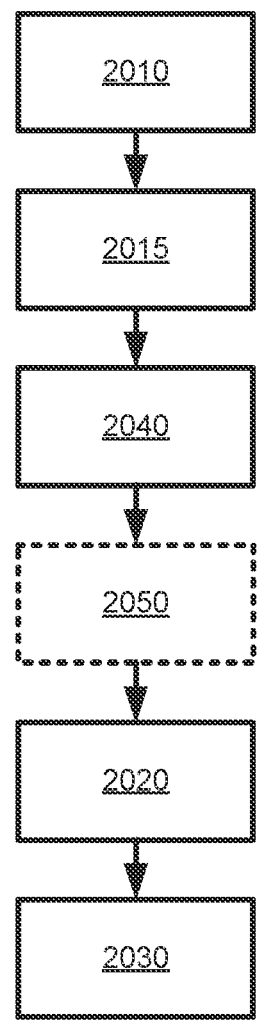
FIG. 3 is a block scheme of a method for accumulating light exposure data to an actual light profile for an individual.

FIG. 3 is a block scheme of a method 2000 for accumulating light exposure data to an actual light profile for an individual.

The method 2000 comprises determining 2010 in which light exposure zone among a plurality of light exposure zones the individual is presently located. The plurality of light exposure zones comprises an indoor light exposure zone. The indoor light exposure zone comprises one or more light sources.

The method 2000 further comprises determining 2015 a distance between a head of the individual and a floor of the indoor light exposure zone in which the individual is determined to be presently located.

The method 2000 further comprises receiving 2040 illumination data for the indoor light exposure zone from the one or more light sources.

The method 2000 further comprises determining 2020 light exposure data for the light exposure zone in which the individual is determined to be presently located. The light exposure data is determined based on the received illumination data from the one or more light sources of the indoor light exposure zone and the determined distance between the head of the individual and the floor of the indoor light exposure zone in case the individual is determined to be presently located in the indoor light exposure zone.

The method 2000 further comprises accumulating 2030 the determined light exposure data to the actual light profile for the individual.

The plurality of light exposure zones may comprise an outdoor light exposure zone.

The method 2000 may further comprise receiving 2050 local weather data for the outdoor light exposure zone from a weather service provider, and the light exposure data may be determined based on the received local weather data of the outdoor light exposure zone in case the individual is determined to be presently located in the outdoor light exposure zone.

The person skilled in the art realizes that the present inventive concept by no means is limited to the preferred variants described above. On the contrary, many modifications and variations are possible within the scope of the appended claims. Additionally, variations to the disclosed variants can be understood and effected by the skilled person in practicing the claimed invention, from a study of the drawings, the disclosure, and the appended claims.

What is claimed is:

1. A light exposure monitoring system comprising:
a central control server;
a plurality of indoor light exposure zones, each indoor light exposure zone comprising one or more light sources, each light source is configured to send illumination data to the central control server; and
a positioning system configured to communicate with the central control server and to determine:
a position of an individual within the plurality of indoor light exposure zones, and
a current distance between a head of the individual and a floor within the plurality of indoor light exposure zones;
wherein the central control server is configured to:
determine in which indoor light exposure zone among the plurality of indoor light exposure zones the individual is presently located based on the determined position of the individual,
determine light exposure data for the indoor light exposure zone, in which the individual is determined to be presently located in, based on the illumination data received from the one or more light sources of the indoor light exposure zone in which the individual is determined to be presently located and the determined current distance between the head of the individual and the floor of the indoor light exposure zone in which the individual is determined to be presently located, and
accumulate the light exposure data to an actual light profile for the individual.

2. The light exposure monitoring system according to claim 1, wherein the positioning system comprises:
one or more distance sensors configured to determine the current distance between the head of the individual and the floor of the indoor light exposure zone in which the individual is determined to be presently located.

3. The light exposure monitoring system according to claim 1, wherein the one or more distance sensors comprises one or more of a radar sensor, a LIDAR sensor, a camera, a time-of-flight camera, and a stereo camera.

4. The light exposure monitoring system according to claim 1, wherein the positioning system is further configured to determine a direction in which the individual is facing, and wherein the central control server is further configured to determine light exposure data further based on the direction in which the individual is facing.

5. The light exposure monitoring system according to claim 1, further comprising:
one or more eye sensors configured to communicate with the central control server and to determine a size of a pupil of an eye of the individual; and
wherein the central control server is further configured to determine light exposure data further based on the size of the pupil of the eye of the individual.

6. The light exposure monitoring system according to claim 5, wherein the one or more eye sensors comprise optical sensors.

7. The light exposure monitoring system according to claim 1, wherein the positioning system comprises:
one or more optical detectors configured to communicate with the central control server, each optical detector being associated with a position within the plurality of indoor light exposure zones, and wherein the one or more optical detectors are configured to detect the individual, thereby determining the position of the individual.

8. The light exposure monitoring system according to claim 1, wherein the positioning system comprises:
one or more electronic devices, each electronic device being associated with a position within the plurality of indoor light exposure zones; and
a portable device associated with the individual, the portable device being configured for wireless communication with the one or more electronic devices; and
wherein the position of the individual is determined based on the wireless communication between the one or more electronic devices and the portable device.

9. The light exposure monitoring system according to claim 8, wherein the one or more electronic devices are further configured for wireless communication with the central control server, and wherein the central control server is further configured to determine the position of the individual based on the wireless communication between the one or more electronic devices and the portable device.

10. The light exposure monitoring system according to claim 8, wherein the portable device is further configured to communicate with the central control server, and to determine the position of the individual based on the wireless communication between the one or more electronic devices and the portable device.

11. The light exposure monitoring system according to claim 1, wherein the one or more light sources comprises adjustable light sources.

12. The light exposure monitoring system according to claim 1, wherein the positioning system is further configured to determine a position for each individual in a plurality of individuals.

13. The light exposure monitoring system according to claim 12, wherein the central control server is further configured to:
determine in which indoor light exposure zone among the plurality of indoor light exposure zones each individual in the plurality of individuals is presently located based on the determined position of each individual;
determine light exposure data for the indoor light exposure zone, in which each individual in the plurality of individuals is determined to be presently located in, based on the illumination data received from the one or more light sources of the indoor light exposure zone in which each individual is determined to be presently located; and
accumulate the light exposure data to an actual light profile for each individual.

14. The light exposure monitoring system according to claim 1, further comprising:
an outdoor light exposure zone; and
wherein the central control server is further configured to:
determine light exposure data for the outdoor light exposure zone, in which the individual is determined to be presently located, based on illumination data associated with the outdoor light exposure zone.

15. The light exposure monitoring system according to claim 14, wherein the illumination data associated with the outdoor light exposure zone is based on local weather data received from a weather service provider.

16. The light exposure monitoring system according to claim 14, wherein the outdoor light exposure zone comprises a light sensor configured to send illumination data associated with the outdoor light exposure zone to the central control server.

17. A central control server comprising:
a control circuitry configured to:
receive a position of an individual;
receive a current distance between a head of the individual and a floor;
determine in which light exposure zone among a plurality of light exposure zones the individual is presently located based on the received position of the individual;
wherein the plurality of light exposure zones comprises an indoor light exposure zone, the indoor light exposure zone comprising one or more light sources;
the control circuitry is further configured to:
receive illumination data from the one or more light sources;
determine light exposure data for the light exposure zone in which the individual is determined to be presently located in, wherein the light exposure data is determined based on the received illumination data from the one or more light sources of the indoor light exposure zone and the current distance between the head of the individual and the floor in case the individual is determined to be presently located in the indoor light exposure zone; and
accumulate the light exposure data to an actual light profile for the individual.

18. The central control server according to claim 17, wherein the plurality of light exposure zones comprises an outdoor light exposure zone, wherein the control circuitry is further configured to:
receive local weather data of the outdoor light exposure zone from a weather service provider; and
wherein the light exposure data is determined based on the local weather data received from the weather service provider in case the individual is determined to be presently located in the outdoor light exposure zone.

* * * * *